(12) United States Patent
Singer

(10) Patent No.: US 8,501,192 B2
(45) Date of Patent: Aug. 6, 2013

(54) USE OF SOLUBLE CEACAM8 FOR DIAGNOSING, TREATING OR MONITORING DISEASES, AND A METHOD FOR SCREENING COMPOUNDS THAT PREVENT APOPTOSIS

(75) Inventor: Bernhard Singer, Essen (DE)

(73) Assignee: Charite Universitaetsmedizin Berlin, Berlin (DE)

( * ) Notice: Subject to any disclaimer, the term of this patent is extended or adjusted under 35 U.S.C. 154(b) by 107 days.

(21) Appl. No.: 12/680,716

(22) PCT Filed: Sep. 26, 2008

(86) PCT No.: PCT/EP2008/062930
§ 371 (c)(1),
(2), (4) Date: Aug. 5, 2010

(87) PCT Pub. No.: WO2009/040418
PCT Pub. Date: Apr. 2, 2009

(65) Prior Publication Data
US 2010/0310458 A1     Dec. 9, 2010

(30) Foreign Application Priority Data
Sep. 27, 2007  (EP) .................................... 07117396

(51) Int. Cl.
*A61K 39/00*     (2006.01)
*A61K 38/14*     (2006.01)
*A61K 38/16*     (2006.01)

(52) U.S. Cl.
USPC .................. 424/198.1; 514/20.9; 514/21.2

(58) Field of Classification Search
None
See application file for complete search history.

(56) References Cited

U.S. PATENT DOCUMENTS

| | | |
|---|---|---|
| 2004/0185053 A1 | 9/2004 | Govindan |
| 2004/0214184 A1* | 10/2004 | Skubitz et al. ............... 435/6 |
| 2005/0037439 A1* | 2/2005 | Bourner et al. ............ 435/7.2 |
| 2007/0140966 A1 | 6/2007 | Chang |
| 2007/0293416 A1* | 12/2007 | Markel ........................... 514/2 |

FOREIGN PATENT DOCUMENTS

WO      03/070266 A     8/2003

OTHER PUBLICATIONS

Fortney et al. "Integrative computational biology for cancer research" Hum Genet 130, 2011, 465-481.*

* cited by examiner

*Primary Examiner* — Daniel E Kolker
*Assistant Examiner* — James Rogers
(74) *Attorney, Agent, or Firm* — Norris McLaughlin & Marcus, P.A.

(57) ABSTRACT

The invention relates to new uses of soluble CEACAM6 or CEACAM8, or substances that are specific to soluble CEACAM8. Another object of the invention concerns the use of CEACAM1-specific and/or CEACAM6-specific compounds for apoptosis prevention in-vitro. The invention also relates to a method for screening compounds, which prevent apoptosis and a method for preventing apoptosis in human granulocytes.

16 Claims, 7 Drawing Sheets

% = cell survival

USE OF SOLUBLE CEACAM8 FOR DIAGNOSING, TREATING OR MONITORING DISEASES, AND A METHOD FOR SCREENING COMPOUNDS THAT PREVENT APOPTOSIS

This application is a 371 application of PCT/EP2008/062930 filed Sep. 26, 2008, which claims priority to the European application 07117396.7 filed Sep. 27, 2007.

The invention relates to new uses of soluble CEACAM6 and/or soluble CEACAM8, or substances that are specific to soluble CEACAM8. Another object of the invention concerns the use of CEACAM1-specific and/or CEACAM6-specific compounds for apoptosis prevention in-vitro. The invention also relates to a method for screening compounds, which prevent apoptosis and a method for preventing apoptosis in human granulocytes.

Granulocytes form the first and fastest line of defense against pathogenic infections. Upon arrival at the site of infection, they participate in the inflammatory reaction by phagocytosis and intracellular killing of bacteria, the production of inflammatory mediators and the release of cytotoxic enzymes and proteins. An unfortunate consequence of granulocyte recruitment represents the ability to cause collateral tissue damage during acute inflammation, and thus their activity and their half-life must be tightly controlled. Their survival is limited by apoptosis, a process that is critical for the resolution of inflammation. Apoptosis refers to a programmed cell death, whereby the cell executes a cell's intrinsic suicide program. It is thought that the apoptosis program is evolutionarily conserved among virtually all multi-cellular organisms. In many cases apoptosis may be a default program that must be actively inhibited in healthy surviving cells. Cell death by apoptotic processes comes along with an early manifestation of membrane asymmetry, which is detected as appearance of phosphatidylserine on the outer leaflet of the plasma membrane, preceding DNA fragmentation, plasma membrane blebbing and the loss of membrane integrity. Normally, granulocytes are short-lived cells with a half-life of only six to twenty hours in circulation undergoing apoptosis subsequently. The decision by a cell to submit to apoptosis is influenced by a variety of regulatory stimuli and environmental factors. Both pro-apoptotic and anti-apoptotic agents alter the lifespan of granulocytes.

It is known that physiological activators of apoptosis include tumor necrosis factor (TNF), Fas ligand (FasL), transforming growth factor A, the neurotransmitters glutamate, dopamine, N-methyl-D-aspartate, withdrawal of growth factors, loss of matrix attachment, calcium and glycocorticoids. Damage-related inducers of apoptosis include heat shock, viral infection, bacterial toxins, the oncogenes myc, rel and E1A, tumor suppressor p53, cytolytic T cells, oxidants, free radicals and nutrient deprivation. Furthermore, therapy-associated apoptosis inducers are known including gamma radiation, UV radiation and a variety of chemotherapeutic drugs, such as cisplatin, doxorubicin, bleomycin, methotrexate and vincristine. In particular, FasL and staurosporine are potent inducers of apoptosis in granulocytes. Contrary, pro-inflammatory cytokines, e.g. GM-CSF, G-CSF and IL-6, can increase the number of polymorphonuclear granulocytes (PMN) by prolonging their lifespan. Membrane-anchored proteins like PECAM-1 are also described to regulate apoptosis in granulocytes. It is a disadvantage of all mentioned inducers that they affect diverse cell types, thereby preventing the selective targeting of cells.

It has been recently shown by Singer et al. (2005) Eur. J. Immunol. 35 (6): 1949-1959, that CEACAM1 triggers the delay of spontaneous and FasL-induced apoptosis in rat granulocytes. That means the ligand binding to CEACAM1 prolongs the lifespan and the functional capacity of granulocytes during an inflammatory reaction. CEACAM1 is a transmembrane-bound glycoprotein which belongs to the CEA-family, which itself is a member of the immunoglobulin super-family. CEACAM1 is abundantly expressed in epithelia, vessel endothelia and leukocytes. Besides CEACAM1, human granulocytes express three other CEA family members, namely CEACAM3 (CD66d, CGM1), CEACAM6 (CD66c, NCA, NCA50/90) and CEACAM8 (CD66b, CGM6, NCA95). It is in contrast to rodent granulocytes that only express CEACAM1. The publication neither provides a tool to prevent a persistent immune response, which is especially undesired in autoimmune diseases, nor adverse effects.

It is known from the disclosure of EP 1 780 220 A1 that substances being specific to membrane-bound CEACAM8 can be used for the prophylactic or therapeutic treatment of human autoimmune diseases and/or gout. CEACAM8 is only expressed in cells of the human granulocyte-lineage, thereby expecting less adverse effects due the exclusive targeting. CEACAM8 is present on the surface of granulocytes as well as stored in the secondary granules of granulocytes. Upon activation, CEACAM8 can be translocated to the plasma membrane from the storage pools within granulocytes. However, the transport and interaction of substances to the cell-immobilized CEACAM8 and a small spectrum of diseases related to granulocytes limit the use.

US 2007/0071758 A1 teaches methods and compositions for the regulation of the immune system. In particular, the lymphocyte activity is regulated in such a manner that the efficacy of tumor-infiltrating lymphocyte therapy is enhanced in the treatment of cancer. For this purpose, a CEACAM1 binding agent is administered, which may comprise a member of the CEACAM protein family. The interaction is assigned to the transmembrane-bound CEACAM1 protein. However, the document lacks a disclosure of potential binding agents and the amino acid sequences thereof, but only notes the binding capability of CEACAM1 itself and CEACAM5 to the CEACAM1 target. Contrary, the inability of CEACAM1 to bind CEACAM6 is demonstrated, which implies the same deficiency in binding to CEACAM8 as CEACAM6 paralogue.

Therefore, the technical problem forming the basis of the present invention is to provide further substances for the treatment of human autoimmune diseases, cancer and several other diseases, especially such substances that improve the efficacy and minimize adverse effects.

The present invention solves this problem by the use of an effective amount of soluble CEACAM6 and/or soluble CEACAM8, or parts thereof, or the DNA encoding said compounds, for the diagnosis, production of a medicament for the prophylactic or therapeutic treatment and/or monitoring of diseases related to granulocytes, B lymphocytes, T lymphocytes, NK cells, monocytes, macrophages, dendritic cells, epithelial cells, endothelial cells and/or liver cells.

CEACAM8 is a glycosylphosphatidylinositol-anchored membrane glycoprotein with a molecular weight of around 95 kDa. It is a member of the CEA family and a product of the CGM6 (NCA-W272) gene. In addition to the membrane-anchored form, a soluble CEACAM8 form is released extracellularly after stimulation. Both CEACAM8 versions comprise an identical amino acid sequence with the exception of a leader sequence labeling the designated membrane-bound CEACAM8. Enzymes that posttranslationally modify CEACAM8 by adding a GPI anchor to fix the protein to the membrane recognize the leader sequence. So far, no ultimate biological function could be identified to the released, soluble CEACAM8 in human.

It is known that PMNs are initially primed by injury and acute inflammations. Priming denotes a distinct cell state, which is characterized by the preparation of the cells to perform their biological task more efficiently. The priming of granulocytes may also be induced by GM-CSF that additionally delays the apoptosis rate and induces new protein synthesis. The priming comes along with an increase in CEACAM8 concentration that has been exclusively assigned to the membrane-anchored CEACAM8 up to now. The inventor has surprisingly demonstrated that the increase in CEACAM8 concentration is based on the enhanced production of soluble CEACAM8, but not membrane-anchored CEACAM8, standing by in granula and being released after another stimulation, e.g. by cytokines from T cells. It has also been found that soluble CEACAM8 strongly binds to CEACAM1 and CEACAM6, but lacks any homophilic CEACAM8-CEACAM8 binding. Thus, soluble CEACAM8 shows an exceeding binding ability in comparison to the membrane-anchored form that mediates heterophilic adhesion only to the closely related CEACAM6 in in-vitro cell-cell adhesion studies. The released, soluble CEACAM8 can interact with all CEACAM1 and/or CEACAM6 expressing cell types, such as epithel, endothel, lymphendothel and all haematopoetic cells (granulocytes, B and T lymphocytes, NK cells, monocytes, macrophages or dendritic cells). The functional role of soluble CEACAM8 is utilized to induce a wide range of functions in the aforementioned disease patterns. In contrast to other CEACAM molecules, CEACAM8 does not bind to bacterial strains carrying Opa-proteins (e.g., Neisseria or Haemophilus).

In diametrical opposition to the teaching of US 2007/0071758 A1, the present inventor has shown the unexpected ability of CEACAM1 to bind CEACAM6. The homophilic interaction as well as the heterophilic interaction with CEACAM1 may be exploited in a similar way as described for the soluble CEACAM8 above.

In addition, the inventor has demonstrated the astonishing effect of soluble CEACAM6 and/or CEACAM8 to co-stimulate proliferation. It is especially directed to human polymorphonuclear granulocytes (PMN) and/or peripheral blood monocytic cells (PBMCs), but other CEACAM1 and/or CEACAM6 expressing cell types can be favorably affected too. In particular, the CEACAM8 triggered cell death is surprisingly prevented by the pre-treatment of human granulocytes with soluble CEACAM8, which is binding to surface-bound CEACAM1 and CEACAM6 on granulocytes. This action is the first ever shown function for soluble CEACAM8. Furthermore, soluble CEACAM6 and/or CEACAM8 may co-activate or co-inhibit B lymphocytes, T lymphocytes, NK cells, monocytes, macrophages, dendritic cells, epithelial cells, endothelial cells and/or liver cells. Notably, CEACAM8 is naturally released from internal granules of PMN in order to manipulate the aforementioned cell types. The secretion of CEACAM8 represents a novel physiological way to induce various functions in all CEACAM1 and/or CEACAM6 expressing cell types. A variety of diseases related to these cell types can be diagnosed, treated and/or monitored therefore.

In more detail, an effective amount of soluble CEACAM6 and/or soluble CEACAM8, or parts thereof, or the DNA encoding said compounds, is used for the diagnosis and/or monitoring of human autoimmune diseases, gout, aberrance of the immune response, cancer and/or infection diseases.

The invention also concerns the use of an effective amount of full length soluble CEACAM6 and/or full length soluble CEACAM8, or the DNA encoding said compounds, for the diagnosis, production of a medicament for the prophylactic or therapeutic treatment and/or monitoring of human gout, cancer and/or infection diseases.

According to the invention, an effective amount of soluble CEACAM6 and/or soluble CEACAM8, or parts thereof, or an effective amount of full length soluble CEACAM6 and/or full length soluble CEACAM8, or the DNA encoding said compounds, is used for the diagnosis, production of a medicament for the prophylactic or therapeutic treatment and/or monitoring of cancer, wherein cancer is diagnosed or monitored by labeling neoangiogenetic blood vessels close to tumors by soluble CEACAM6 and/or CEACAM8.

Soluble CEACAM6 and soluble CEACAM8 can be used either separately or together. If the effect of a single use of soluble CEACAM6 and CEACAM8 is approximately identical, the use of soluble CEACAM8 is preferred. CEACAM8 cannot be inactivated by storage and the like due to the lack of homophilic interaction. A synergistic effect may be achieved by using both compounds. In the latter case, the compounds can be used either simultaneously or sequentially.

Soluble CEACAM6 and/or CEACAM8 also comprise variants, mutants, parts of the proteins or homologous sequences having the same function. A couple of methods are known to the skilled artisan to generate equivalent proteins, i.e. proteins that are analog in function to those of the inventive teaching. Therefore, the invention also contains the aforementioned modifications. For example, mutants can be generated by substitution, deletion, insertion, translocation, inversion and/or addition of at least a single amino acid. It is known that certain amino acids exhibit similar physicochemical characteristics making the substitution among each other possible. Variants of the CEACAM proteins can arise from modifications, such as alkylation, arylation or acetylation of at least a single amino acid, from incorporation of enantiomers and/or from fusion of the CEACAM proteins with a single or multiple amino acids, a peptide or a protein. It is preferred in the meaning of the invention that CEACAM6 and/or CEACAM8 are fused to a purification tag for affinity chromatography. Parts of the CEACAM proteins relates to a restriction to those regions that are sufficient for the expression of a specific function. All alterations are inevitably limited by the requirement of preserving the function. However, the parts of the CEACAM proteins can be very small due to the characterization of the binding site, which also triggers the signal cascade. In the meaning of the invention, it is to be clearly distinguished between CEACAM parts of any size and homologous sequences which homology is related to the entire CEACAM protein. Preferably, the homology between natural soluble CEACAM6 or CEACAM8, respectively, and a derivative thereof having the same features amounts to at least 60%, more preferably 75%, most preferably 90%. Similarly, the homology is to be considered if the aforementioned part of any size is altered to a variant or mutant. In addition, several techniques are described in prior art to generate non-homologous peptides with the same function. The present teaching if solving the problem of the invention covers all peptide derivatives, which are developed on the basis of the present ingredients by such procedures.

The present invention also relates to DNA encoding soluble CEACAM6 and/or CEACAM8 for the diagnosis, production of a medicament for the prophylactic or therapeutic treatment and/or monitoring of human autoimmune diseases, gout, aberrance of the immune response, cancer and/or infection diseases. The prior teaching of the present specification concerning the amino acid sequences and derivatives thereof is valid and applicable without restrictions to the underlying DNA.

Preferably, the soluble CEACAMs of the invention are recombinantly expressed and purified. Therefore, the construct can be fused with a tag for affinity chromatography, such as Strep-tag, His-tag, GST-tag, Arg-tag or the calmodulin binding protein (CBP). For instance, CBP binds to a calmodulin resin, e.g. to be used as column matrix. The column is loaded with the protein suspension and all components lacking CBP are immediately eluted. After removal of unspecific binders by washing steps, the CBP-fused construct is removed from the column. Alternatively, the DNA encoding the protein sequences can be obtained, amplified, altered or synthesized with techniques known to the skilled artisan. Subsequently, the DNA can be introduced into a vector and transcribed and translated in cells.

In a preferred embodiment of the invention, a construct combining soluble CEACAM6 or CEACAM8 with the human Fc part is used. cDNA encoding soluble extracellular domains of CEACAM6 or CEACAM8, respectively, fused to a human heavy chain Fc domain can be generated by PCR using appropriate cDNA molecules and specific primer combinations. The fragments are cloned into expression vectors, which are transfected into such human cells that are well established for the production of Fc constructs, such as HEK293 cells. The cell culture supernatant is taken to isolate the secreted CEACAM6-Fc or CEACAM8-Fc, respectively, via protein G sepharose columns, and the constructs are finally dialyzed. The Fc region is an effector of the complement cascade but is not involved in antigen binding of an antibody. The purification tag does not cause any immune response in humans and may kept linked to the active ingredient of CEACAM6 or CEACAM8, respectively. Consequently, the downstream processing is simplified by omitting the cleavage step. If the handling or application requires a single CEACAM molecule of interest, the Fc region can be enzymatically cleaved off by means of papain enzyme, and the sole CEACAM6 or CEACAM8 is purified by FPLC.

The soluble CEACAM6 and/or CEACAM8 are preferably used for the therapeutic treatment. A therapeutically relevant effect relieves to some extent one or more symptoms of a disease, aberrance and/or acute gout attack or returns to normality, either partially or completely, one or more physiological or biochemical parameters associated with or causative of the disease or pathological conditions. Monitoring is considered as a kind of treatment provided that the compounds are administered in distinct intervals, e.g. in order to booster the proliferation response and eradicate the symptoms of the disease completely. Either the identical compound or different compounds can be applied. In the meaning of the invention, prophylactic treatment is advisable against acute gout attacks, or if the subject possesses any preconditions for the outbreak of an autoimmune disease, cancer or infection diseases, such as a familial disposition, a genetic defect, a previously passed disease, or a previous or expected contact with a source of infection.

Autoimmune diseases concern an exaggerated immune reaction directed against the body's tissue, which is aberrantly assigned as deleterious target. Severe inflammations are caused by autoimmune diseases, which finally result in the damage of the affected organs. In an embodiment of the present invention, the soluble CEACAM6 and/or CEACAM8 are used for the production of a medicament for the prophylactic or therapeutic treatment of arthritis, arthrosis, autoimmune hepatitis, chronic gastritis, colitis, such as colitis ulcerosa, diabetes mellitus type I, Morbus Crohn, Multiple Sclerosis, neurodermatitis, pancreatitis, psoriasis and/or rheumatism, preferably arthritis, arthrosis, chronic gastritis, Morbus Crohn, neurodermitis, pancreatits, rheumatism and/or psoriasis, more preferably arthritis, arthrosis, rheumatism and/or psoriasis, most preferably arthrosis, rheumatism and/or psoriasis.

In another embodiment of the invention, an effective amount of soluble CEACAM6 and/or soluble CEACAM8, or parts thereof, or the DNA encoding said compounds, is used for the production of a medicament for diagnosis and/or monitoring of the immune response. Herein, both the congenital (non-adaptive, innate, unspecific) and the acquired (adaptive specific) immune response may be modulated. It is particularly preferred that the immune response of peripheral blood monocytic cells (PBMC) is modulated. Since T cells play an important role in transplant rejection, such a modulation towards a lower response level can favorably prevent rejection reactions. Besides the alteration of the normal immune response, the modulation can also be applied to treat pathogenic aberrances of the immune response. Depending on the kind of aberrance, the immune response is either enhanced for better individual's protection or dropped to stop self-damage. Especially the latter intervention is used to inactivate hyperactive granulocytes efficiently.

Soluble CEACAM6 and/or CEACAM8 according to the invention can preferably be used in prophylaxis, diagnosis, follow-up and/or treatment of tumor diseases. Furthermore, it is preferred to use the molecules in the prophylaxis and/or treatment of cancer diseases, including tumors and metastases. In a preferred embodiment the cancerous disease or tumor being treated or prophylactically prevented, or whose reappearance is prevented, is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases. More specifically, the tumors may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in-situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Leydig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phylloides; hemangiosarcoma; lymphangiosarcoma; myxosarcoma, ovarian carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia.

In a preferred embodiment of the present invention, soluble CEACAM8 exerts an influence on the neoangiogenesis of endothelial cells, i.e. the generation of new endothelial cells and/or lymphendothelial cells. In adults, neoangiogenesis and neolymphangiogenesis usually occur in such vessels induced by the tumor. Furthermore, endothelial cells only express CEACAM1 if stimulated to grow. Soluble CEACAM8, which has the highest affinity to CEACAM1, may be used for targeting of drugs by conjugating CEACAM8 to a chemotherapeutic. The chemotherapeutic may comprise a cytokine, a chemokine, a pro-apoptotic, interferon, a radioactive moiety, or combinations thereof, and moderates nucleic acid metabolism, protein metabolism, cell division, DNA replication, purine biosynthesis, pyrimidine biosynthesis, amino acid biosynthesis, gene expression, mRNA processing, protein synthesis, apoptosis, or combinations thereof.

In addition to the therapeutic treatment of tumors, soluble CEACAM8 is preferably used in cancer diagnosis by labeling neoangiogenetic vessels, particularly blood vessels in the surrounding of a tumor. Diagnosis denotes the recognition of a clinical picture by means of a detectable moiety. The labels of CEACAM8 depends on its inherent features and the detection methods to be applied and are well known to the skilled artisan. Examples of suitable detection methods according to the present invention are luminescence, VIS coloring, radioactive emission, electrochemical processes or magnetism. The diagnostic method of the invention can be performed in a simple and fast manner.

Soluble CEACAM6 and/or CEACAM8 are also used for diagnosis, therapy and/or monitoring of defense and abatement of pathogens, particularly infectious diseases. In the meaning of the invention, an "infectious disease" is a clinically evident disease that damages or injures the host, which results from the presence of one or more pathogenic agents comprising viruses, viroids, bacteria, fungi, protozoa, multicellular parasites, or aberrant proteins known as prions. These pathogens can cause diseases in both animals and plants. Transmission of an infectious disease may occur through several pathways, including through contact with infected individuals, by water, food, airborne inhalation, or through vector-borne spread. In the course of the detrimental colonization of a host organism by a foreign pathogen, the infecting organism seeks to utilize the host's resources to multiply. The infecting pathogen interferes with the normal functioning of the host and can lead to chronic wounds, gangrene, loss of an infected limb, and even death. The host's response to infection is inflammation. The CEACAM6 and/or CEACAM8 protein can be either administered to prevent the infection of a mammal with a pathogen and the outbreak of the disease in advance, or to treat the disease caused by the infectious agent. The approach aims at a prompt effect, i.e. to cure the given infection sickness as quickly as possible or to protect against a viral infection immediately.

Another object of the invention is a pharmaceutical composition comprising as active ingredients an effective amount of soluble CEACAM6 and/or soluble CEACAM8, or parts thereof, or the DNA encoding said ingredients, optionally together with pharmaceutically tolerable adjuvants. A "pharmaceutical composition" in the meaning of the invention is any agent in the field of medicine, which can be used in prophylaxis, diagnosis, therapy, follow-up or aftercare of patients who suffer from autoimmune diseases, gout, aberrance of the immune response, cancer and/or infection diseases in such a way that a pathogenic modification of their overall condition or of the condition of particular regions of the organism could establish at least temporarily.

The active CEACAMs of the invention may be fused or complexed with another molecule that promotes the directed transport to the destination, the incorporation and/or distribution within the target cell.

The terms "effective amount" or "effective dose" or "dose" are interchangeably used herein and denote an amount of a pharmaceutical compound having a prophylactically or therapeutically relevant effect on a disease or pathological conditions. A prophylactic effect prevents the outbreak of a disease or even the infection with a pathogen after the infiltration of single representatives such that the subsequent propagation of the pathogen is strictly diminished, or it is even completely inactivated. A therapeutically relevant effect relieves to some extent one or more symptoms of a disease or returns to normal either partially or completely one or more physiological or biochemical parameters associated with or causative of the disease or pathological conditions. The respective dose or dosage range for administering the pharmaceutical composition according to the invention is sufficiently high in order to achieve the desired prophylactic or therapeutic effect of reducing tobacco abuse. It will be understood that the specific dose level, frequency and period of administration to any particular human will depend upon a variety of factors including the activity of the specific compound employed, the age, body weight, general health, sex, diet time of administration, route of administration, rate of excretion, drug combination and the severity of the specific therapy. Using well-known means and methods, the exact dose can be determined by one of skill in the art as a matter of routine experimentation.

The composition of the invention is produced in a known way using common solid or liquid carriers, diluents and/or additives and usual adjuvants for pharmaceutical engineering and with an appropriate dosage depending on the intended mode of application. These pharmaceutically acceptable excipients comprise salts, buffers, fillers, chelating agents, antioxidants, solvents, bonding agents, lubricants, tablet coatings, flavor additives, flavors, preservatives and suspending agents. In the meaning of the invention, an "adjuvant"

denotes every substance that enables, intensifies or modifies a specific immune response against soluble CEACAM6 and/or CEACAM8 if administered simultaneously, contemporarily or sequentially. Known adjuvants for injection solutions are for example aluminum compositions, such as aluminum hydroxide or aluminum phosphate, saponins, such as QS21, muramyldipeptide or muramyltripeptide, proteins, such as gamma-interferon or TNF, M59, squalen or polyols. The amount of excipient material that is combined with the active substance to produce a single dosage form varies depending upon the host treated and the particular mode of administration.

Soluble CEACAM6 and/or CEACAM8 are adapted in forms which are suitable for oral administration, such as tablets, film tablets, lozenges, capsules, pills, powders, solutions, dispersions, suspensions or depot forms thereof, for transdermal administration, such as solutions, suspensions, creams, ointments, gels, emulsions or band-aids, for parental administration, such as suppositories, and for intravenous infusion, subcutaneous injection or intramuscular administration, examples for the latter three are solutions and suspensions. The substances can also be adapted for topical, transmucosal, transurethal, vaginal, rectal or pulmonary administration in the appropriate formulations given above.

Depending upon the manner of introduction, the compounds may be formulated in a variety of ways. The concentration of therapeutically active ingredients in the formulation may vary from about 0.1 to 100 wt %. The solution may be administered alone or in combination with other treatments. In a preferred embodiment, the CEACAM proteins to be injected are in a water-soluble form, such as a pharmaceutically acceptable salt, which is meant to include both acid and base addition salts. The injection solution may also include one or more of the following: carrier proteins, such as serum albumin, buffers, stabilizing agents, coloring agents, and the like. Additives are well known in the art, and they are used in a variety of formulations.

Moreover, the teaching of the present specification concerning the use of soluble CEACAM6 and/or CEACAM8 is considered as valid without restrictions to the pharmaceutical composition if these CEACAMs are applicable therein.

The invention also relates to the use of substances being specific to soluble CEACAM8 for the production of a medicament for the prophylactic or therapeutic treatment of diseases related to granulocytes, B lymphocytes, T lymphocytes, NK cells, monocytes, macrophages, dendritic cells, epithelial cells, endothelial cells and/or liver cells. The use of such substances directed against soluble CEACAM8 inhibits the functional effects triggered by soluble CEACAM8 that is naturally released by activated granulocytes in response to diverse stimuli. Therefore, the use of specific substances to soluble CEACAM8 represents another way for treatment in addition to the way using specific substances to membrane-anchored CEACAM8. As a specific substance to soluble CEACAM8 binds and inactivate soluble CEACAM8 and blocks its function, such as the proliferate effect, the substances being specific to membrane-anchored CEACAM8 can unhamperedly perform the induction of apoptosis. The dual impact results in a particular effective knockout of granulocytes, which shows a synergistic yield. Beyond the inhibition of proliferation, other functions can be efficiently stopped. The interception of soluble CEACAM8 modulates the immune response and may eliminate the neoangiogenesis or the accumulation of T cells within a center of inflammation. For example, an over-reaction of the immune system in a sick knee, which is full of blood or water due to a trauma or gout, respectively, is diminished or even completely prevented.

In an embodiment of the present invention, the substances being specific to soluble CEACAM8 are used for the production of a medicament for the prophylactic or therapeutic treatment of cancer and/or infection diseases. The teaching of the present specification concerning the aforementioned clinical pictures in the context of using soluble CEACAM6 and/or CEACAM8 is considered as valid and applicable without restrictions to the use of substances being specific to soluble CEACAM8 if expedient, particularly to the use with opposite intention.

The term "specific substances" as used herein comprises molecules with high affinity to soluble CEACAM8 or variants thereof in order to ensure a reliable binding. The degree of variation between native CEACAM8 and its variants is inevitably limited by the requirement of recognition by the specific substances. The binding site on the target of soluble CEACAM8, which is recognized by a specific substance, can be a definite small region, such as an epitope to be bound by an antibody. Such a region can be either used as isolated molecule or inserted into other proteins than CEACAM8. These regions and epitopes, respectively, are also included in soluble CEACAM8 variants that are a target of CEACAM8-specific substances in the meaning of the invention. Substances being specific to soluble CEACAM8 comprise nucleic acids, peptides, proteins, carbohydrates, polymers and small molecules having a molecular weight between 50 and 1.000 Da. The proteins or peptides are preferably selected from the group consisting of antibodies, cytokines, lipocalins, receptors, lectins, avidins, lipoproteins, glycoproteins, oligopeptides, peptide ligands and peptide hormones. The nucleic acids are preferably single or double stranded DNA or RNA, oligonucleotides, aptamers or Spiegelmers, or parts thereof. Preferred examples of low molecular weight ligands are steroids. Suitable specific substances are described in detail in EP 1 780 220 A1, which is incorporated as reference in the disclosure of the invention hereby.

Since the effects of substances being specific to membrane-anchored CEACAM8 and substances being specific to soluble CEACAM8 are interrelated, it is possible to apply substances that are specific to CEACAM8 in general. By doing so, substances being mono-specific to CEACAM8 are preferably used for the production of a medicament for the prophylactic or therapeutic treatment of human autoimmune diseases, gout, aberrance of the immune response, cancer and/or infection diseases. The term "mono-specific" denotes a mode of binding which is characterized by the exclusive recognition of a single target. The mono-specific substances used in the present invention only recognize the CEACAM8 target or variants thereof. The receptor/ligand-interaction is featured by high affinity, high selectivity and minimal or even none cross-reactivity to other target molecules, particularly other CEACAMs. Unhealthy and harmful impacts on other cell types bearing other CEACAMs are advantageously overcome by the mono-specific binding to CEACAM8. For instance, CEACAM8-specific substances do not interfere with epithelia, endothelia, dendritic cells, NK cells, monocytes, macrophages, B-lymphocytes or T-lymphocytes. In an embodiment of the present invention, the mono-specific substances are the monoclonal antibodies mAb 80H3, mAb B13.9, mAb B4-EA4, mAb BIRMA 17C, mAb BL-B7, mAb G10F5, mAb MF25.1, mAb 12-140-5, mAb JML-H16, mAb Kat4c, mAb TET2, mAb YG-C46A8, mAb YG-051B9, mAb C76G4 and/or mAb YG-C94G7, preferably mAb 80H3, mAb B13.9, mAb B4-EA4, mAb BIRMA 17C, mAb BL-B7, mAb G10F5, JML-H16 and/or mAb MF25.1, more preferably mAb 80H3 and/or mAb B13.9, most preferably mAb 80H3. The code designations of the monoclonal antibodies refer to the clone name in the HLDA (human leukocyte differentiation antigens) Antibody Database. In another embodiment of the invention, the substances are polyclonal antibodies, preferably Polyclonal Rabbit anti-human Carcinoembryonic Antigen.

In a preferred embodiment of the invention, substances being able to discriminate between the membrane-anchored form and the soluble form of CEACAM8 are used. Herein, the use of mono-specific binding substances refers to the exclusive recognition of unmodified soluble CEACAM8, but no posttranslational modifications thereof, such as a GPI anchor-bearing version.

It is still another object of the present invention to use compounds being specific to CEACAM1 and/or CEACAM6 for the prevention of apoptosis in human granulocytes in-vitro. Ligand binding to membrane-anchored CEACAM8 mimicked e.g. by the monoclonal antibody 80H3 leads to a significant induction of apoptosis in human granulocytes, whereas antibodies binding to CEACAM1, CEACAM3 and CEACAM6 do not alter the percentage of surviving PMNs. For the first time, the inventor has revealed that the CEACAM8 triggered cell death is prevented by pre-treatment of human granulocytes with compounds that bind to surface-bound CEACAM1 and CEACAM6 on granulocytes. Thus, it is preferred that the compounds are specific to membrane-anchored CEACAM1 and/or membrane-anchored CEACAM6. In an embodiment of the invention, the compounds are selected from the group of nucleic acids, peptides, carbohydrates, polymers, small molecules having a molecular weight between 50 and 1.000 Da, and proteins, preferably antibodies, cytokines and lipocalins. In a preferred embodiment of the invention, the compounds are soluble CEACAM8, monoclonal antibodies and/or polyclonal antibodies, or parts thereof, or the DNA encoding said compounds. Particularly preferred monoclonal antibodies are mouse anti-CEACAM1 mAb 4/3/17 and/or anti-CEACAM6 mAb 13H10. A preferred soluble CEACAM8 is soluble human CEACAM8-Fc. The prior teaching of the present specification concerning the use of soluble CEACAM8 for the diagnosis, production of a medicament for the prophylactic or therapeutic treatment and/or monitoring is considered as valid and applicable without restrictions to the in-vitro use of the compound for apoptosis prevention if expedient.

If using equimolar amounts of substances, which are specific to membrane-anchored CEACAM8, for apoptosis induction and compounds being specific to CEACAM1 and/or CEACAM6, the survival rate is at least 80% in comparison to a control that is not treated with the apoptosis inducing substances, preferably at least 90%, more preferably at least 100%, most preferably at least 110%. It shall be understood that the survival rate is a relative measure being related to a control, which survival is inherently less than 100%. In consequence of the proliferate effect of the inventive compounds, both the induced apoptosis and the inherently undergoing apoptosis are thwarted, which may result in data beyond 100% compared to the control. In a preferred embodiment, the data are applicable to equimolar amounts of anti-CEACAM8 mAb 80H3 and soluble CEACAM8-Fc and granulocytes following five hours of incubation.

The invention consequently relates to a method for stimulating the proliferation of cells by incubating a human cell sample with at least one compound being specific to CEACAM1 and/or CEACAM6. In an embodiment of the invention, the human sample comprises PBMCs, which are cultivated with soluble CEACAM6 and/or soluble CEACAM8 as compounds being specific to CEACAM1 and CEACAM6. The proliferation rate is significantly increased, preferably at least 40%, more preferably at least 65%, most preferably at least 85%. Further details of the material and experimental procedure are given in the examples, which are especially preferred. The substances are of particular efficacy in stimulating proliferation if pre-stimulated cells are used.

Further, the invention may be practiced as a method for preventing apoptosis in human granulocytes by incubating a human sample comprising granulocytes with at least one compound being specific to CEACAM1 and/or CEACAM6, and specific incubation products are formed, thereby preventing apoptosis. The sample is withdrawn from a human to be examined following good medical practice. In the present invention, the sample preferably consists of blood, serum, plasma, saliva or urine. It is also possible to gather a tissue sample by biopsy. The sample may be purified to remove disturbing components, such as inhibitors for the formation of hydrogen bonds, or the granulocytes can be concentrated in the sample. Downstream processing and/or concentrating are performed by routine techniques, such as centrifugation or gel filtration. It is recommended to combine several methods for better yields. The human cell sample is stored, such as frozen, cultivated for a certain period or immediately incubated with compounds that are specific to CEACAM1 and/or CEACAM6, or variants thereof. Incubation denotes the contacting of specific compounds with CEACAM1 and/or CEACAM6, which can be realized without a chemical conversion, e.g. antibody-CEACAM binding, or may involve a biochemical reaction, e.g. by an enzyme-CEACAM complex. Adding chemical solutions and/or applying physical procedures, e.g. impact of heat, can improve the accessibility of granulocytes and/or CEACAM proteins in the sample. Cultivation and incubation of granulocytes are known to those skilled in the art following standard procedures. As result of the incubation, specific incubation products comprising compound-CEACAM1-complexes and/or compound-CEACAM6-complexes are formed. It is preferred that the compounds are specific to membrane-anchored CEACAM1 and/or CEACAM6.

The granulocytes may be either susceptible to apoptosis themselves, i.e. they naturally undergo apoptosis, or exposed to pro-apoptotic substances. The apoptotic processes, which are prevented, can be monitored by the techniques described in the ongoing course of the present specification. This in-vitro method is preferably applied to samples of humans suffering from an autoimmune disease. Testing of several specific compounds makes the selection of that compound possible that is best suited for the treatment of the human subject. The in-vivo dose rate of the chosen compound is advantageously pre-adjusted to the apoptosis susceptibility of the specific granulocytes with regard to their in-vitro data. Therefore, the therapeutic efficacy is remarkably enhanced. Preferably, a mono-specific compound is selected. More preferably, the compound is soluble CEACAM8, or parts thereof, or the DNA encoding said compound, most preferably soluble human CEACAM8-Fc. The prior teaching of the present specification concerning the use of soluble CEACAM8 for the diagnosis, production of a medicament for the prophylactic or therapeutic treatment and/or monitoring as well as the use of CEACAM1-specific and/or CEACAM6-specific compounds for preventing apoptosis in human granulocytes in-vitro is considered as valid and applicable without restrictions to the method for preventing apoptosis in human granulocytes if expedient.

Another object of the present invention is a method for treating diseases related to granulocytes, B lymphocytes, T lymphocytes, NK cells, monocytes, macrophages, dendritic cells, epithelial cells, endothelial cells and/or liver cells, wherein an effective amount of at least one substance being specific to soluble CEACAM8 is administered to a human in need of such treatment. It is still another object of the invention to provide a method for treating diseases related to granulocytes, B lymphocytes, T lymphocytes, NK cells, monocytes, macrophages, dendritic cells, epithelial cells, endothelial cells and/or liver cells, wherein an effective amount of soluble CEACAM6 and/or CEACAM8, or parts thereof, or the DNA encoding said compounds, is administered to a human in need of such treatment. The prior teaching of the present invention and embodiments thereof is considered as valid and applicable without restrictions to the methods of treatment if expedient.

Furthermore, the invention teaches a method for screening compounds, which prevent apoptosis comprising the steps of:
providing a cell sample being capable of expressing membrane-anchored CEACAM8 and membrane-anchored CEACAM1 and/or membrane-anchored CEACAM6,
dividing the sample into portions,
incubating at least one portion with compounds to be screened,
incubating the portion with a at least one substance being specific to membrane-anchored CEACAM8,
comparing the apoptosis rate in the portion with another portion that is not incubated with the compounds, and
detecting the specific binding of compounds to membrane-anchored CEACAM1 and/or membrane-anchored CEACAM6 that prevent apoptosis.

A method is known from WO 03/002764 A2 that teaches the identification of therapeutically useful compounds by detecting the expression of glycoprotein antigens of the CEACAM family. However, the method addresses the alteration of expression of any CEACAM member in order to increase the susceptibility for apoptosis. Contrary to that, the present inventor discloses a method for screening compounds to prevent apoptosis. These compounds do not interfere with the expression of the gene or gene product of any CEACAM molecule but block the function of the gene product, which has been additionally specified to be membrane-anchored CEACAM1 and/or CEACAM6.

The inventive method makes the identification of compounds possible, which exert an influence on the signal cascade via CEACAM1 and/or CEACAM6 and increase proliferation, which comes along with the decrease of the apoptosis rate of cells. The cell sample refers to primary cells or genetically engineered cells. The latter are capable of expressing membrane-anchored CEACAM8 by transfection with appropriate vectors harboring the CGM6 (NCA-W272) gene or parts thereof. Furthermore, the genetically engineered cells are capable of expressing membrane-anchored CEACAM1 and/or CEACAM6 by transfection with appropriate vectors. Preferably, the recombinant cells are of eukaryotic origin. The primary cells are human granulocytes, which are preferred in the screening method of the invention. The human granulocytes can also be established as cell line. Furthermore, cell homogenates or tissue extracts containing cells that express membrane-anchored CEACAM8 and CEACAM1 and/or CEACAM6 can be used. The cell sample is divided into multiple portions. At least two portions are provided; one is used for screening while the other one serves as negative control. Preferably, the number of portions for screening exceeds the number of control portions. Usually, numerous portions are subjected to a high-throughput screening.

The compounds to be screened in the inventive method are not restricted anyway. In an embodiment of the invention, the compounds are selected from the group of nucleic acids, peptides, carbohydrates, polymers, small molecules having a molecular weight between 50 and 1.000 Da, and proteins, preferably antibodies, cytokines and lipocalins. These compounds are often available in libraries. The prior teaching of the present specification concerning the use of CEACAM1/6-specific compounds for preventing apoptosis in human granulocytes in-vitro is considered as valid and applicable without restrictions to the method for screening such substances that prevent apoptosis if expedient. It is preferred to incubate a single compound within a distinct portion of the cell sample. However, it is also possible to investigate the cooperative effect of compounds by incubating at least two compounds within one portion. A further portion of cells is simultaneously incubated in the absence of the compounds. The incubation process of cells depends on various parameters, e.g. the cell type and the sensitivity of detection, which optimization follows routine procedures known to those skilled in the art.

In the next step of the inventive method, the cells are treated to become apoptotic. The portions are incubated with at least one substance that is specific to membrane-anchored CEACAM8. In an embodiment of the invention, the substances are selected from the group of nucleic acids, peptides, carbohydrates, polymers, small molecules having a molecular weight between 50 and 1.000 Da, and proteins, preferably antibodies, cytokines and lipocalins. In a preferred embodiment of the present invention, the substances are monoclonal antibodies, preferably mAb 80H3, mAb B13.9, mAb B4-EA4, mAb BIRMA 17C, mAb BL-B7, mAb G10F5, mAb MF25.1, mAb 12-140-5, mAb JML-H16, mAb Kat4c, mAb TET2, mAb YG-C46A8, mAb YG-051B9, mAb C76G4 and/or mAb YG-C94G7, more preferably mAb 80H3, mAb B13.9, mAb B4-EA4, mAb BIRMA 17C, mAb BL-B7, mAb G10F5 and/or mAb MF25.1, most preferably mAb 80H3 and/or mAb B13.9. In another preferred embodiment of the invention, the substances are polyclonal antibodies, preferably Polyclonal Rabbit anti-human Carcinoembryonic Antigen.

The identification of effective compounds in the meaning of the invention is directly performed by determining the survival rate, apoptosis rate or the rate constant of apoptosis kinetics, respectively. Therefore, the number of viable cells or the number of apoptotic cells, respectively, is measured at a particular time. Common methods of the art comprise staining with annexin V and/or propidium iodide, or the measurement of nucleosomes released during apoptosis by means of a sandwich ELISA. Another method records immunochemically the caspase-induced proteolysis of cytokeratins and the produced neo-epitopes of this filamentous protein. The measured values are related to the cell number at the beginning of the experiment and to the period of incubation. The higher the number of apoptotic cells after a certain period, the higher is the initial apoptosis rate or the rate constant, respectively. The calculated apoptosis rates, constants, apoptotic or viable cell numbers of the compound-incubated portions are compared with the negative control. A compound that prevents apoptosis is indicated by any value of cell survival exceeding the corresponding value of the negative control, or any value of cell death falling below the corresponding value of the negative control.

Among those compounds being revealed to prevent apoptosis each or some representatives are selected for further analysis. Preferably, the compounds showing the greatest discrepancy to the control are chosen. They are analyzed for specificity to membrane-anchored CEACAM1 and/or CEACAM6 to exclude another signal transduction, which is not initiated by CEACAM receptor binding, and additionally tested for such a cross-reactivity that may prevent apoptosis by linked pathways if simultaneous docking to further receptors occurs. Several methods are known in the field of the art for detecting specific and/or mono-specific binding, such as gel shift experiments, Biacore measurements, X-ray structure analysis, competitive binding studies, and the like. In a preferred embodiment of the present invention, the mono-specific binding to membrane-anchored CEACAM1 and/or CEACAM6 of substances preventing apoptosis is detected.

Alternatively, cells that are not able of expressing CEACAM1 and CEACAM6, but being able of expressing membrane-anchored CEACAM8, can serve as negative control, which is subjected to the compounds. In this way apoptosis cannot inevitably be affected via CEACAM1 or CEACAM6. Any decreased susceptibility to apoptosis in the negative control is caused by another pathway than that the present invention is based on. It is required that the different cell types which are used either for screening or as control show a comparable half-life and apoptosis behavior, the latter being characterized by similar features of the apoptotic cells, which should be favorably detected by the same method. CEACAM1/6-defective cells can be originated from primary cells, cell lines, recombinant cells, cell homogenates and tissue extracts. For example, CEACAM1/6 deletion mutants of human granulocytes are used as negative control. This modified method requires the incubation of each compound at least twice. Preferably, an equal number of trials for actual screening and for the control experiment is applied. Assessing the abolishment of apoptosis susceptibility and the compound specificity to CEACAM1 and/or CEACAM6 in parallel compensates the higher number of trials. The direct analysis of compound specificity may be further improved by providing cell portions that are capable of expressing membrane-anchored CEACAM1 and CEACAM8, as well as cell portions being capable of expressing membrane-anchored CEACAM6 and CEACAM8. The assessment is performed by correlating the survival or apoptosis, respectively, in the parallel trials with the survival or apoptosis in a portion of CEACAM1/6-defective cells, which is incubated in the absence of compounds (so called negative control of the negative control). That means the CEACAM1/6-defective cells are necessarily divided into multiple portions in advance. Desired compounds in the meaning of the invention are indicated by any higher level of viable cells in the cell portions expressing CEACAM8 and CEACAM1 and/or CEACAM6 in comparison with both levels of viable cells in the CEACAM1/6-defective cell portions, which are incubated either with compounds or not, whereby the latter levels in the portions of CEACAM1/6-defective cells have to be equivalent.

In a further aspect of the invention, an effective amount of soluble CEACAM8 or parts thereof, or the DNA encoding said compound, are used for B- or T-cell expansion. In a preferred embodiment, soluble CEACAM8 or parts thereof, or the DNA encoding said compound, is used in combination with other compounds which may be co-stimulatory or have another effect on B- and/or T-cells.

In a further aspect of the invention, an effective amount of soluble CEACAM8, or parts thereof, or the DNA encoding said compound, is used for treatment of patients with immunodeficiency as a result of chronic or acute infection and/or chemo- or radiation therapy.

It was surprisingly found that contacting B- or T-cells with an efficient amount of soluble CEACAM8 or parts thereof, or with DNA encoding said compound, lead to an efficient expansion of the respective cells. In this respect, the term "expansion" is to be understood as a measure for cell proliferation and/or cell activation of the respective cells.

If a patient suffers from low B- or T-cell numbers or is expected to suffer from it, it is common medical practice, to isolate a sample of the respective cells, expand these cells in vitro and transfer the expanded cells back to the same patient or a patient which is compatible with the first patient or to a patient which is treated in parallel with immuno-suppressive agents.

This is of particular interest in situations, where primary B- or T-cells are derived from a patient prior to or accompanying an incident which may have an influence on the immune system of said patient, like e.g. chronic or acute infection and/or chemo- or radiation therapy. In such a setting, primary B- or T-cells are isolated from a patient and cultured in vitro under conditions which allow for expansion of these cells. In the meantime, the patient e.g. will be treated with radiotherapy and when the treatment is finished, the expanded B- or T-cells are transplanted back to the patient.

In particular, an effective amount of soluble CEACAM8, or parts thereof, or the DNA encoding said compound, is used in adoptive immunotherapy.

In adoptive immunotherapy, e.g. T cell-based cytotoxic responses are used to attack cancer. In brief, T cells that have a natural or genetically engineered reactivity to a patients' cancer are expanded in vitro using a variety of means and then adoptively transferred into a cancer patient. T cells with a natural occurring reactivity to a patient's cancer can be found infiltrated in the patients' own tumors. The tumor is harvested, and these tumor infiltrating lymphocytes (TIL) are expanded in vitro using high concentrations of interluekin-2 (IL-2), anti-CD3 and allo-reactive feeders. These T cells are then transferred back into the patient along with exogenous administration of IL-2. Thus far, a 51% objective response rate has been observed; in some patients, tumors shrank to indetectable size. In the case of engineered T cells, T cell receptors (TCR) that have been identified to have reactivity against tumor associated antigens are cloned into a replication incompetent virus that is capable of genomic integration. A patients own lymphocytes are exposed to these viruses and then expanded non-specifically or stimulated using the engineered TCR. The cells are then transferred back into the patient. This therapy has been demonstrated to result in objective clinical responses in patients with refractory stage 1V cancer. The Surgery Branch of the National Cancer Institute (Bethesda, Md.) is actively investigating this form of cancer treatment for patients suffering aggressive melanomas.

It was now found that soluble CEACAM8 is efficient in promoting the expansion in vitro of primary or engineered B- or T-cells.

The invention is also directed to a method for in vitro B- or T-cell expansion comprising the steps:
a) providing B- or T-cells;
b) bringing B- or T-cells in contact with an efficient amount of soluble CEACAM8, or parts thereof, or with the DNA encoding said compound;
c) culturing B- or T-cells.

If need be, the method may comprise the additional step of cryopreserving the cells of step c).

In a further aspect, the invention is directed to B- or T-cells that have been expanded according to the method outlined above.

The invention is further directed to soluble CEACAM8 or parts thereof for use in the manufacture of a medicament with a shelflife of more than 4 weeks.

Shelflife is a crucial parameter of every medicament. If the shelflife is short, the medicament will be more expensive, because it cannot be prepared in large quantities and stored, but needs to be manufactured on demand and distributed quickly. A shelflife of more than 4 weeks allows for an economically interesting manufacturing and distribution system and as such enables the provision of medicaments comprising soluble CEACAM8 or parts thereof.

The invention has several advantages: In the scope of the invention, soluble CEACAM6 and/or soluble CEACAM8 have been characterized for the first time, resulting in the provision of a pharmaceutical composition for the diagnosis, production of a medicament for the prophylactic or therapeutic treatment and/or monitoring of human autoimmune diseases, gout, aberrance of the immune response, cancer and/or infection diseases. Depending on the desired effect, either soluble CEACAM6 and/or CEACAM8 are used to positively affect the functions of membrane-bound CEACAM1 and/or CEACAM6 or substances directed against soluble CEACAM6 and/or CEACAM8, particularly CEACAM8, are used to negatively affect the functions of membrane-bound CEACAM1 and/or CEACAM6.

Secreted, soluble CEACAM6 as well as CEACAM8 bind to other CEACAMs expressed on various cell types and potentially modulates their functions, such as proliferation, activation, apoptosis and the like. The aforementioned effects of proliferation and apoptosis are interrelated such that the apoptotic effect caused by specific substances to membrane-anchored CEACAM8 is prevented. This is the first function found for soluble CEACAM8. After exposed to a stimulus, soluble CEACAM8 is secreted and able to bind a variety of cells, such as T cell, B cell, NK cell, granulocytes, dendritic cells, endothelia and epithelia. Consequently, the use of soluble CEACAM8 is a promising, novel method for a broad spectrum of therapies as well as in the diagnostic use. The interaction with T cells is of special benefit to efficiently inactivate stimulated granulocytes. In contrast to the prior art of EP 1 780 220 A1, the granulocytes are not directly attacked, but the T cells and the T cell mediated activation of granulocytes, respectively, which trigger the autoimmune impulse, are influenced. Any negative action of granulocytes is advantageously scotched.

The principle underlying the invention is the unexpected binding of soluble CEACAM6 and CEACAM8 to membrane-anchored CEACAM1 and CEACAM6. Therefore, soluble CEACAM6 or CEACAM8 may be substituted by any compound having specificity to CEACAM1 and/or CEACAM6 and triggering the same functions thereby, such as the prevention of apoptosis in human granulocytes in-vitro. Such compounds can be favorably screened by applying the screening method of the invention.

The membrane-anchored targets CEACAM1 and/or CEACAM6 as well as the membrane-anchored target CEACAM8 trigger opposite functions. The simultaneous performance of catching a ligand, which is specific to CEACAM1 and/or CEACAM6, and providing another ligand, which is specific to CEACAM8, enhances the functional efficacy synergistically. The present invention makes both actions possible by a single substance being an antibody directed against CEACAM8.

All compounds and substances are characterized by a high affinity, specificity and stability; low manufacturing costs and convenient handling. These features form the basis for a reproducible action, wherein the lack of cross-reactivity is included, and for a reliable and safe interaction with their matching target structures.

It is to be understood that this invention is not limited to the particular methods, pharmaceutical compositions or uses described herein, as such matter may, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a substance" includes one or more different substances and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used.

FIGURES

EXAMPLES

Figure 1:
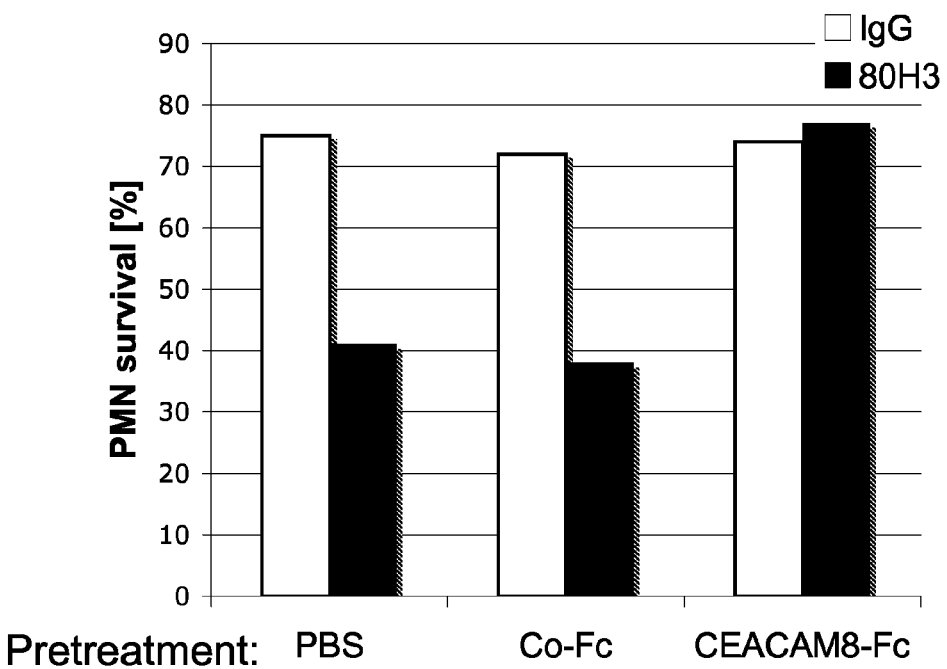
FIG. 1 shows the alteration of apoptosis rate in human granulocyte, which is triggered by membrane-bound CEACAM8 and inhibited by pre-treatment with soluble CEACAM8-Fc.

Example 1 cDNA encoding soluble extracellular domains of CEACAM8 fused to a human heavy chain Fc domain (huCEACAM8-Fc) were generated by PCR, using appropriate cDNA molecules and specific primer combinations: cDNA fragments for CEACAM8 and Fc were cloned sequentially into the HindIII-EcoRI sites and EcoRI-XhoI sites (Fc) of the pcDNA3.1(+) expression vector (Invitrogen, San Diego, Calif.), sequenced and transfected into HEK293 cells. The principle of generating such constructs is described by Singer et al. (2005) Eur. J. Immunol. 35 (6): 1949-1959, which is incorporated as reference in the disclosure of the invention hereby. The Fc chimerical proteins were accumulated in serum-free Pro293s-CDM medium (BioWhittaker, Walkersville. Md.) for 10 days and were recovered by Protein A/G-Sepharose affinity chromatography. Endotoxin levels of antibody and Fc-construct preparations were determined using the Pyrogent plus Gel-Clot assay (BioWhittaker) and were found to be below the detection limit of 0.06 U/ml. The construct huCEACAM6-Fc was obtained in a similar way.

The membrane-anchored CEACAM8 was previously described to mediate heterophilic adhesion exclusively to the closely related CEACAM6 in in-vitro cell-cell adhesion studies but no homophilic binding activity was found. Here, it was demonstrated for the first time that soluble CEACAM8 is strongly binding to CEACAM1 and CEACAM6 but again is lacking any homophilic CEACAM8-CEACAM8 binding. Biacore results in Table 1 show the homophilic binding of CEACAM1 and CEACAM6 with the relative unit (RU) of 110 and 50, respectively. There was no homophilic binding of soluble CEACAM8. The binding of CEACAM1 as analyte (=immobilized on the Biacore chip) and CEACAM8 as ligand (=flashed over in the soluble form) showed the far highest binding (1490 RU). CEACAM6 as ligand seemed to be the best interaction partner for CEACAM8 as analyte (780 RU).

TABLE 1

Biacore results of different CEACAM molecules interacting among each other.

|         |         | ligand  |         |         |
|---------|---------|---------|---------|---------|
|         |         | CEACAM1 | CEACAM6 | CEACAM8 |
| analyte | CEACAM1 | 110 RU  | 42 RU   | 340 RU  |
|         | CEACAM6 | 20 RU   | 50 RU   | 1490 RU |
|         | CEACAM8 | 52 RU   | 780 RU  | 0 RU    |

Thus, released, soluble CEACAM8 can interact with all CEACAM1 and/or CEACAM6 expressing cell types, namely epithel, endothel, lymphendothel and all haematopoetic cells (granulocytes, B and T lymphocytes, NK cells, monocytes, macrophages, dendritic cells) as shown in Table 2.

TABLE 2

Various cell types are receptors for CEACAM8 (and CEACAM6).

|                     | CEACAM1 | CEACAM6 | CEACAM8 |
|---------------------|---------|---------|---------|
| Lymphocyte          | +       | +       | −       |
| Granulocyte         | +       | +       | +       |
| NK cell             | +       | −       | −       |
| Dendritic cells     | +       | −       | −       |
| Monocyte/Macrophage | +       | −       | −       |
| Liver cells         | +       | −       | −       |
| Endothelial cells   | +       | −       | −       |
| Epithelial cells    | +       | +       | −       |
| Mast cells          | +       | −       | −       |

Example 2

Materials were obtained from Sigma (Taufkirchen, Germany), unless stated differently. Complete culture medium consisted of RPMI 1640 (Gibco-Life Technology, Eggenstein, Germany) supplemented with 2 mM L-glutamine (Gibco), 100 U/ml penicillin (Gibco), 100 µg/ml streptomycin (Gibco) and 10% heat-inactivated FCS (Gibco). Mouse monoclonal antibody binding to CEACAM8 (mAb 80H3) was obtained from Immunotech, (Marseille, France). Mouse monoclonal antibody binding to CEACAM1 (4/3/17) and the monoclonal antibody binding to CEACAM6 (mAb 13H10) were a gift of F. Grunert (Institute for Immunobiology, Freiburg, Germany, now Genovac). Mouse monoclonal antibody binding to CEACAM3 (mAb Col-1) was obtained from Schlom (National Cancer Institute, Bethesda, Md., US).

Granulocytes were isolated from heparinized (5 U/ml) peripheral blood of rats and healthy donors. After erythrocyte sedimentation through Plasmasteril (Fresenius, Bad Homburg, Germany), PMNs and PBMCs of the leukocyte-rich plasma were separated by gradient centrifugation via Ficoll-Paque (Amersham). The remaining erythrocytes in the pelleted fractions were lysed by repeated suspension in cold 0.2% NaCl solution for 20 seconds followed by washing with cold PBS. More than 96% of the remaining cells were granulocytes as judged by morphological criteria and FACScan analyses using a specific differentiation marker for PMN. Cell viability was >97%, as determined by trypan blue staining.

Granulocytes were re-suspended in RPMI medium at a final concentration of 100.000 cells in a final volume of 100 µl. The cells were then incubated at 37° C. for 5 to 6 hours with or without mouse monoclonal antibodies (30 µg/ml) as indicated. To determine and distinguish between early and late apoptotic/necrotic cells, a procedure based on double staining for annexin V and propidium iodide (PI) was adopted. Annexin V binds to phosphatidylserine, which appears in the outer leaflet of the plasma membrane in early apoptotic cells. In late apoptotic cells, the plasma membrane becomes permeable and allows uptake of PI, which intercalates into DNA. Thus, annexin V labels both early and late apoptotic cells, whereas PI only labels late apoptotic/necrotic cells. Labeling with FITC-coupled annexin V and PI was performed according to the manufacturer's protocol (Bender MedSystems, Vienna, Austria). The labeled cells were analyzed by flow cytometry in a FACScan instrument and the CellQuest software (BD Biosciences).

Following 10 min pre-incubation with PBS, control Fc (30 µg/ml) or CEACAM8-Fc (30 µg/ml), granulocytes were cultured for 5 hours in the presence of isotype-matched control Ig (white column) or the anti-CEACAM8 mAb 80H3 (30 µg/ml, black column). The percentage of cell survival was assessed by double staining with FITC-annexin V/propidium iodide and flow cytometry as described. Exploring the function of membrane-anchored CEACAM8, its effect on apoptosis in freshly isolated granulocytes was tested using the monoclonal antibody mAb 80H3 to mimic the ligand binding. 80H3 is known to bind specifically to CEACAM8 but not to any further CEACAM molecules. The apoptosis in human granulocytes isolated from healthy donors was evidently increased following 5 hours incubation with the monoclonal antibody 80H3 (anti-CEACAM8, approximately 40% versus approximately 73% in the control). That means, CEACAM8 induces apoptosis in human PMNs. However, soluble CEACAM8 is preventing this effect caused by mAb 80H3. Representative results are shown in FIG. 1.

Example 3

Figure 2:
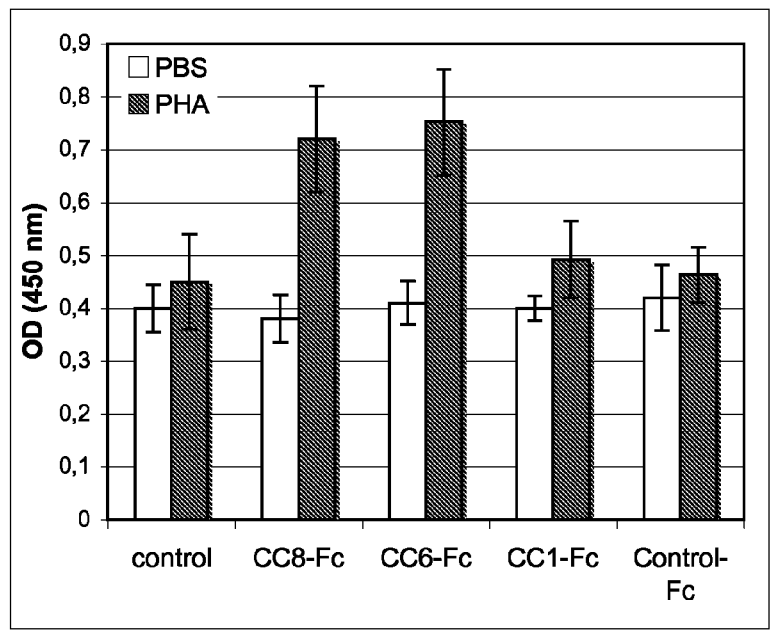
FIG. 2 shows the co-stimulation of proliferation of PBMCs by soluble CEACAM6 or CEACAM8.
Figure 3:
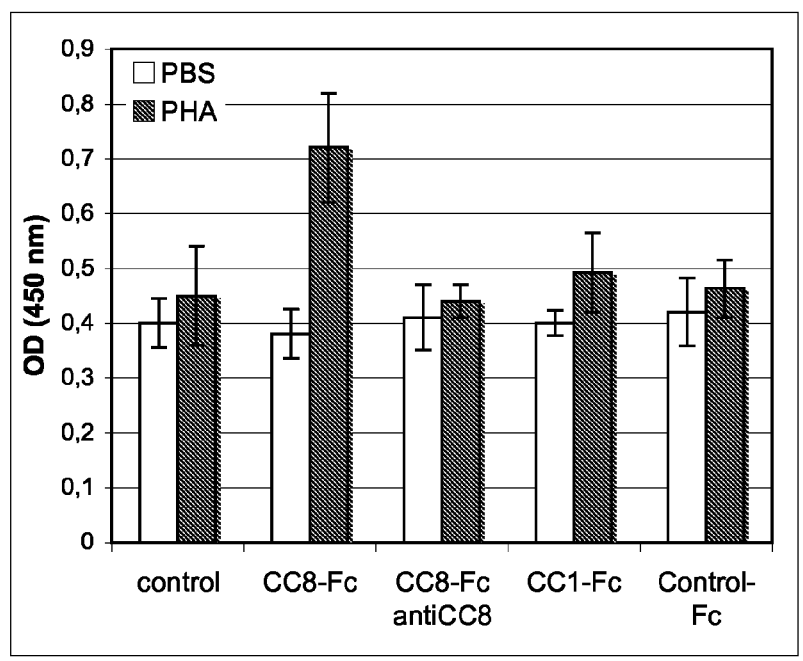
FIG. 3 shows the co-stimulation of proliferation of PBMCs by soluble CEACAM8, and the abolishment of the co-stimulatory effect by an antibody binding to soluble CEACAM8.

The soluble CEACAM8 and CEACAM6 co-stimulate the proliferation of peripheral blood monocytic cells (PBMCs): freshly isolated PBMCs were incubated in the presence or absence of PHA for 3 days. Thereafter, the proliferation was assessed by CellTiter 96 Aqueous one solution reagent (Promega) according to manufacturer's protocol. In the presence of soluble CEACAM8-Fc or CEACAM6-Fc, but not in the presence of CEACAM1-Fc or control protein-Fc, the proliferation rate is significant increased (FIG. 2). Parallel treatment of the cells incubated with CEACAM8-Fc and together with a specifically soluble CEACAM8-binding antibody abolished the co-stimulatory effect (FIG. 3).

Example 4

It is well accepted that CEACAM1 is a homophilic (binding to itself) and heterophilic (binding to CEACAM5, CEACAM6 and, as newly shown by us in this patent application, CEACAM8) cell-cell adhesion receptor molecule (Singer, B. B. CEACAM1. *UCSD-Nature Molecule Pages* (doi:10. 1038/mp. a003597. 01) (2005). In contrast, CEACAM8 is not interacting in a homophilic way. Therefore it is assumed, that long time storage of CEACAM1 disables its ligand binding potential. To that end, the binding capacity of CEACAM1-Fc and CEACAM8-Fc was analyzed, either of relatively fresh isolated (1 week at 4° C.) or long time stored (at least 4 month at 4° C.) samples.

Flow Cytometric Analysis of CEACAM1-Fc and CEACAM8-Fc Binding:

Hela, Hela-CEACAM1 or human dermal endothelial cells (HDEMEC) ($5 \times 10^5$) were incubated for 1 h at 4° C. with human CEACAM1-Fc and CEACAM8-Fc (30 µg/ml, diluted in 3% FCS/PBS), respectively, washed with ice-cold PBS and incubated with FITC-conjugated anti-human Fc F(ab)$_2$. Background fluorescence was determined using not binding ratCEACAM1-Fc. In some cases, control staining with a CEACAM1 specific antibody (clone 283340, R&D systems) was performed. The samples were measured in a flow cytometer (BD Biosciences, San Diego, Calif.) and the data were analyzed using the CellQuest software. Dead cells identified by PI staining were excluded from the determinations.

Figure 4:
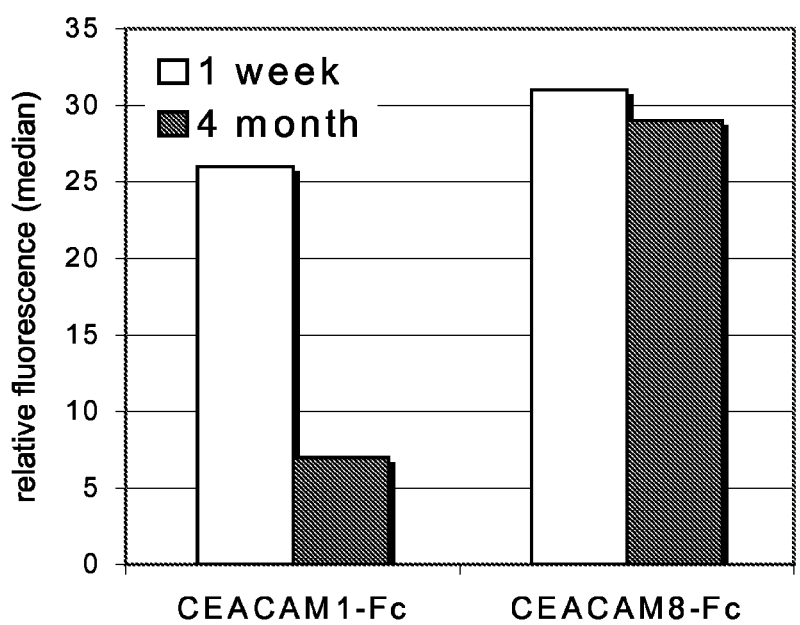
FIG. 4 shows the improved shelflife of soluble CEACAM8 over soluble CEACAM1.

As shown in FIG. 4, shelflife of soluble CEACAM8 is prolonged in comparison to shelflife of soluble CEACAM1. After 4 weeks of storage, soluble CEACAM8 revealed reactivity comparable to reactivity after one week of storage, whereas reactivity of soluble CEACAM1 decreased significantly over time. Thus, soluble CEACAM8 can be used in the manufacture of a medicament with a reasonable shelflife, in particular with a shelflife of more than 4 weeks.

Example 5

In contrast to quiescent endothelial cells, activated, growing endothelial cells express CEACAM1 on their cell surface. In adults, such neo-endothelial growth is induced in early stages of tumor development. Therefore, the targeting of membrane bound CEACAM1 with soluble CEACAM8 as ligand may qualify for diagnosic purposes (e.g. coupled to iron or iron loaded beads for MRT or air/gas filled for ultrasound sonication) as well as for the manufacture of therapeutic drugs (e.g. coupled to radioactivity, cytotoxic agense, drug filled micro- and nano bubbles).

Flow Cytometric Analysis of CEACAM1-Fc and CEACAM8-Fc Binding:

Hela, Hela-CEACAM1 or human dermal endothelial cells (HDEMEC) ($5 \times 10^5$) were incubated for 1 h at 4° C. with human CEACAM1-Fc and CEACAM8-Fc (30 µg/ml, diluted in 3% FCS/PBS), respectively, washed with ice-cold PBS and incubated with FITC-conjugated anti-human Fc F(ab)$_2$. Background fluorescence was determined using not binding ratCEACAM1-Fc. In some cases, control staining with a CEACAM1 specific antibody (clone 283340, R&D systems) was performed. The samples were measured in a flow cytometer (BD Biosciences, San Diego, Calif.) and the data were analyzed using the CellQuest software. Dead cells identified by PI staining were excluded from the determinations.

Figure 5:
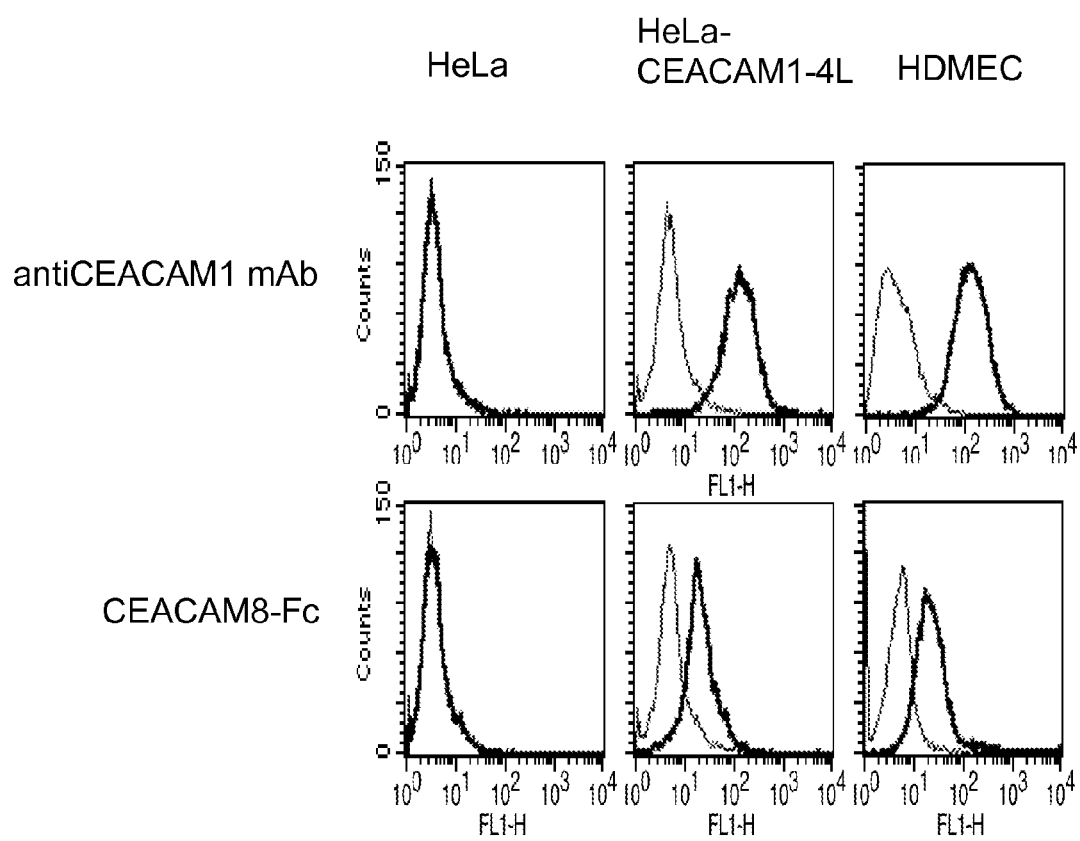
FIG. 5 shows the CEACAM1 specific binding of soluble CEACAM8 to CEACAM1 expressing HeLa cells and HDMECs.

As shown in FIG. 5, soluble CEACAM8 protein binds specifically to CEACAM1 expressing HeLa cells and HDMEC (human proliferating microvascular endothelial cells). Data not shown: HUVEC (human umbilical vein endothelial cells) do not express CEACAM1 and soluble CEACAM8 is not binding to HUVEC. Interestingly cancer cells induce neoangiogenesis mainly via HDMECs and not HUVECs. Therefore, soluble CEACAM8 can be applied as diagnostic agent to detect e.g. neoangiogenetic endothelial cells. Therefore, the targeting ligand, soluble CEACAM8, can be used for diagnosis, e.g. coupled to iron or iron loaded beads for MRT or air/gas filled structures for sonication, as well as for the manufacture of therapeutic drugs, e.g. coupled to radioactivity, cytotoxic agent, drug filled micro- and/or nano-bubbles.

Examples 6

Most recently it was published that soluble CEA (also known as CEACAM5) induces apoptosis in human the epithelial cell line HT29 (Nittka S, Böhm C, Zentgraf H, Neumaier M.: The CEACAM1-mediated apoptosis pathway is activated by CEA and triggers dual cleavage of CEACAM1. Oncogene. 2008 Jun. 12; 27(26):3721-8). Therefore, it was analyzed whether soluble CEACAM8 revealed similar pro-apoptotic properties.

Induction and Analysis of Apoptosis in HDMECs and A549 Cells:

HDMECs and A549 cells were seeded in a 12-well plate and incubated in the presence or absence of control Fc-protein (1 µg/ml 10% FCS/DMEM), CEA (1 µg/ml 10% FCS/DMEM), or CEACAM8-Fc (1 µg/ml 10% FCS/DMEM) alone or in combination as indicated for 24 h in a 5% $CO_2$ humidified atmosphere at 37° C. Then, cells were collected by trypsinization, washed in 10% FCS/DMEM and kept on ice until further use. To determine and distinguish between early and late apoptotic cells, we adopted a procedure based on double-staining for annexin V and PI. Annexin V binds to PS, which appears in the outer leaflet of the plasma membrane in early apoptotic cells. In late apoptotic cells, the plasma membrane becomes permeable and allows uptake of PI, which intercalates into DNA. Thus, annexin V labels both early and late apoptotic cells, whereas PI only labels late apoptotic cells. Labeling with FITC-coupled annexin V and PI was performed according to the manufacturer's protocol (Immunotools, Germany). The labeled cells were analyzed by flow cytometry in a FACScan instrument using the CellQuest software (BD Biosciences).

Figure 6:
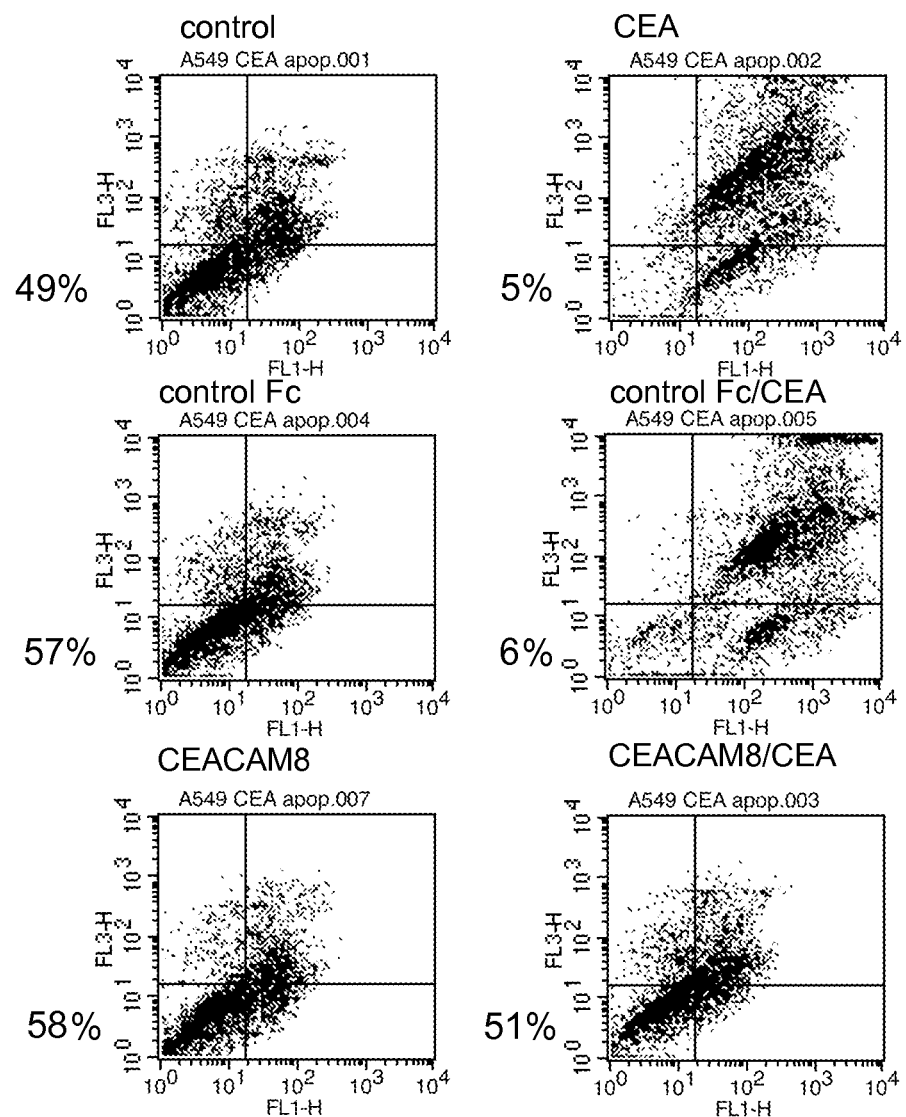
FIG. 6 shows the effect of soluble CEACAM8 on CEA induced apoptosis of A549 cells.

As shown in FIG. 6, cultivation of the epithelial cell line A549 for 24 h in the presence of CEACAM8 did not alter the number of living cells compared with the untreated cells or the Fc control (cell survival: 49%, 57%, 58%). In contast, CEA treatment clearly induced apoptose (cell survival 5%). Interestingly, the incubation of CEA in the presence of soluble CEACAM8 prevented the induction of apoptosis (cell survival 51%), an effect not seen in the sample probed with CEA in the presence of control Fc (cell survival 6%).

Example 7

To investigate the effect of soluble CEACAM8 in activated, proliferating microvascular endothelia (HDMECs), cells were incubated for 24 h in the presence or absence of soluble CEACAM8 and measurement was performed as outlined above.

Figure 7:
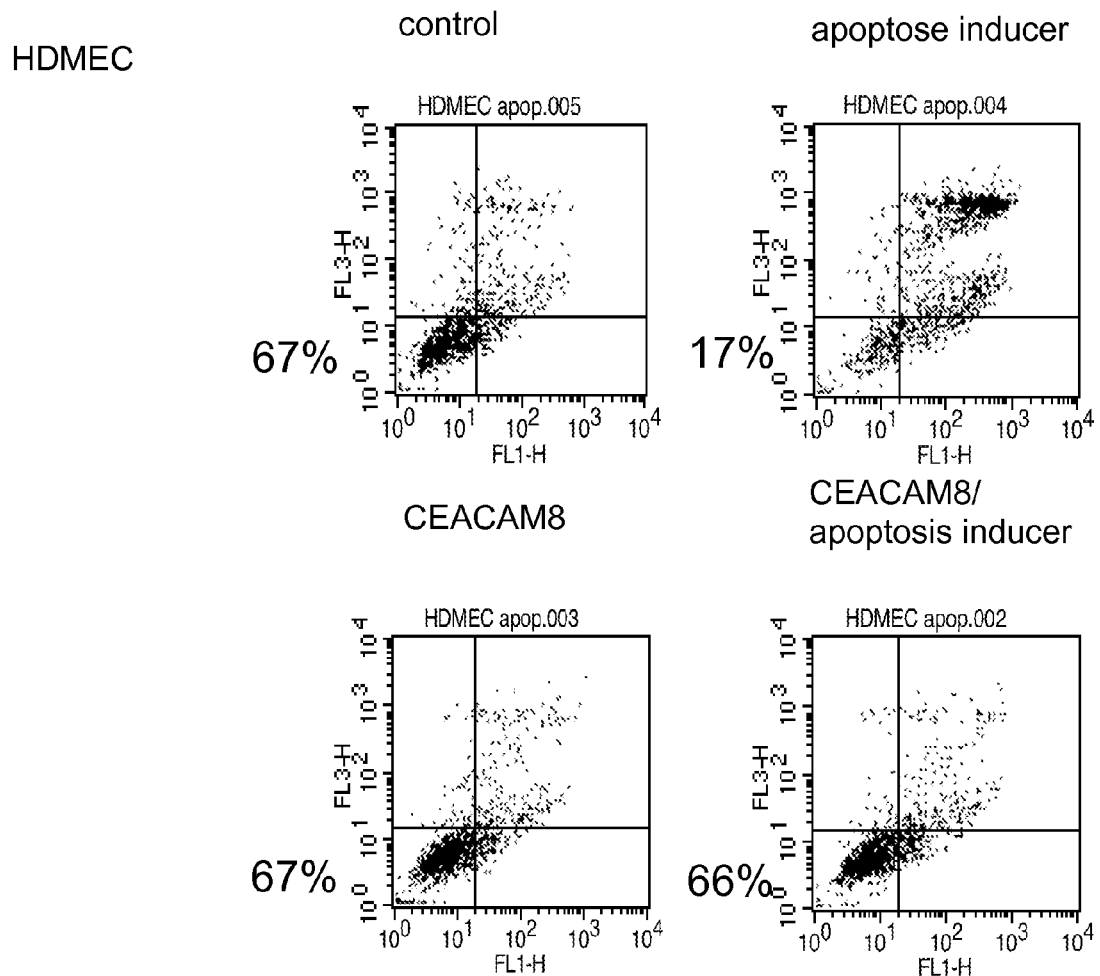
FIG. 7 shows the effect of soluble CEACAM8 on induced apoptosis of HDMEC.

As shown in FIG. 7, soluble CEACAM8 did not alter the number of living cells compared with the untreated control (both 67%). Thus, CEACAM8 itself had no negative effect on endothelial cells. Thus, possible negative effects during the therapeutic utilization of soluble CEACAM8 could be ruled out for the endothelial system. Interestingly, in the presence of an apoptose-inducing agent soluble CEACAM8 significantly increased the fraction of living cells to 66% compared to apoptosis inducer alone (17%).

This finding reveals for the first time an anti-apoptotic effect of soluble CEACAM8 in human endothelial cells. Furthermore, this effect could be prevented by pre-incubation of the samples with CEACAM8 specific antibodies (21%). Taken together, these findings reveal a novel functional role of soluble CEACAM8 in endothelial cells which leads to a so far unrecognized endothelial strategy in preventing endothelial cell death and vessel destruction usually occurring as effect during an inflammatory response and various stages of cancer development.

Example 8

The recognition of Antigens by immune receptors initiates the activation of mature T and B cells during an adaptive immune response. However, full scale B-cell and T-cell activation requires not only B-cell receptor (BCR) and T-cell receptor (TCR) engagement with antigen, but also costimulatory signals provided e.g. in the case of B-cells by T helper cells through the CD40-CD40 ligand (CD40L) interaction. Thus, signaling through the cell surface molecule CD40 is known to play an important role in the proliferation and differentiation of B-lymphocytes. Nevertheless, also B cells are important for T-cell receptor (TCR) costimulation, because they possess functional characteristics of innate immune cells, as they can present Antigens to T cells. Here, it is shown for the first time a co-receptor modulation of BCR and TCR signaling triggered by soluble CEACAM8, a glycoprotein specifically released by granulocytes in response to activation.

B-Cell Expansion Assay:

PBMCs from healthy donors were prepared by gradient centrifugation via Ficoll-Paque. Cells were resuspended in RPMI 1640 (Biochrom) supplemented with 10% (v/v) heat-inactivated FCS (Invitrogen Life Technologies), 3 mM L-glutamine, 0.01 M HEPES, 100 U/ml penicillin, and 100 µg/ml streptomycin (all from Sigma-Aldrich) and incubated overnight before stimulation. All reagents were tested in regard to endotoxin contamination. PBMCs ($2.5 \times 10^4$) at 0.2 ml/well (triplicates) were stimulated for three days in 96 well flat bottom microtiter plates with CD40, anti-human IgG$^+$ IgM$^+$IgA F(ab')$_2$ (Jackson ImmunoResearch), CEACAM8-Fc, ratCEACAM1-Fc (non binding control) alone and in various combinations as indicated in the figure legends or left untreated. Cell proliferation was assessed by CellTiter 96 Aqueous one solution reagent (Promega) according to the manufacturer's protocol. Absorbance was detected at 490 nm in a Sunrise-ELISA reader (Tecan).

T-Cell Expansion Assay:

PBMCs from healthy donors were prepared by gradient centrifugation via Ficoll-Paque. Cells were resuspended in RPMI 1640 (Biochrom) supplemented with 10% (v/v) heat-inactivated FCS (Invitrogen Life Technologies), 3 mM L-glutamine, 0.01 M HEPES, 100 U/ml penicillin, and 100 µg/ml streptomycin (all from Sigma-Aldrich) and incubated overnight before stimulation. All reagents were tested in regard to endotoxin contamination. PBMCs ($2.5 \times 10^4$) at 0.2 ml/well (triplicates) were stimulated for three days in 96 well flat bottom microtiter plates with CD3 (clone MEM-57, Immunotools, Germany), anti-human CD28 (clone 12E8, Immunotools, Germany), CEACAM8-Fc, ratCEACAM1-Fc (non binding control) alone and in various combinations as indicated in the figure legends or left untreated. Cell proliferation was assessed by CellTiter 96 Aqueous one solution reagent (Promega) according to the manufacturer's protocol. Absorbance was detected at 490 nm in a Sunrise-ELISA reader (Tecan).

Figure 8:
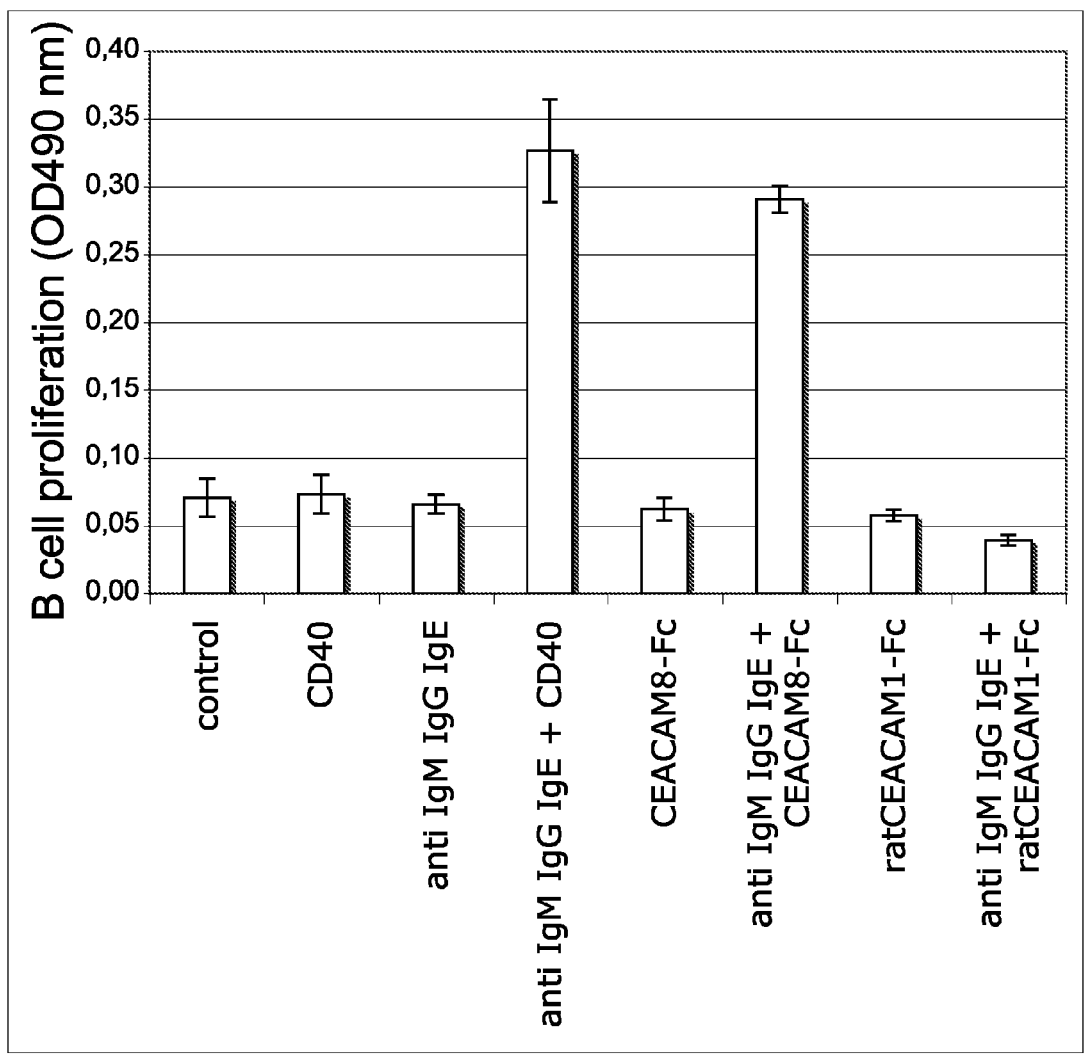
FIG. 8 shows the effect of soluble CEACAM8 on B-cell expansion.

As shown in FIG. 8, B-lymphocytes can be expanded in vitro through treatment of the cells with soluble CEACAM8-Fc in combination with goat polyclonal anti IgM-IgG-IgE antibody. The co-stimulatory effect of soluble CEACAM8 was nearly as efficient as the well-established, co-stimulatory effect of CD40 in combination with anti IgM-IgG-IgE. CEACAM8-Fc alone, CD40 alone, ratCEACAM1-Fc and ratCEACAM1-Fc in combination with anti IgM-IgG-IgE showed no effect.

Figure 9:
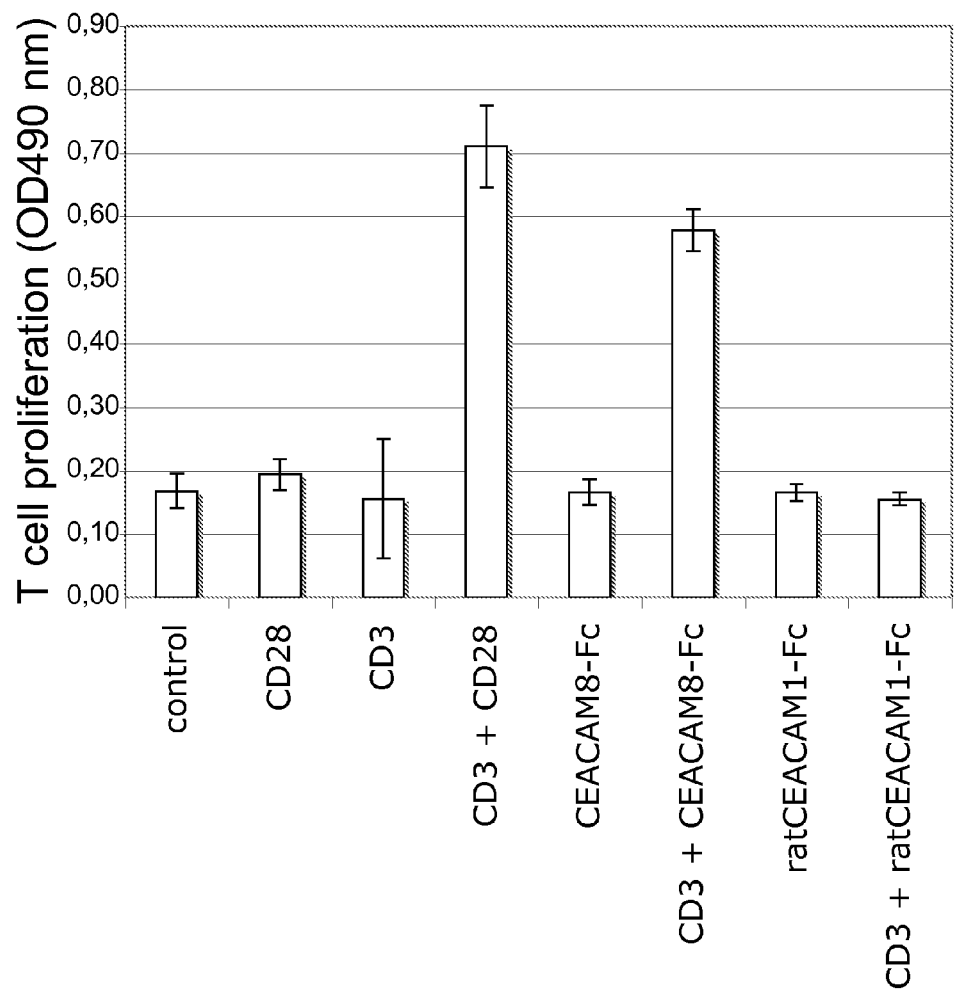
FIG. 9 shows the effect of soluble CEACAM8 on T-cell expansion.

As shown in FIG. 9, T-lymphocytes can be expanded in vitro through treatment of the cells with soluble CEACAM8-Fc in combination with mouse monoclonal CD3 antibody. The co-stimulatory effect of soluble CEACAM8 was nearly as efficient as the well-established, co-stimulatory effect of CD28 in combination with anti CD3. CEACAM8-Fc alone, CD3 alone, CD28 alone, ratCEACAM1-Fc and rat-CEACAM1-Fc in combination with anti CD3 showed no effect.

The soluble CEACAM8-triggered B- and T-cell expansion may be applied as a future immunotherapy to strengthen immunodeficient patients, patients with severe chronical or acute infections and patients undergoing a chemo- or radiation therapy.

The expanded B-lymphocytes and T-lymphocytes can be cryopreserved and the cryopreserved material may be used for at least 5 years later.

The invention claimed is:

1. Method for B- or T-cell expansion, comprising the step of contacting B- or T-cells with full-length soluble CEACAM8 or a DNA encoding said full-length soluble CEACAM8, in an effective amount resulting in B- or T-cell expansion.

2. Method of claim 1, wherein said full-length soluble CEACAM8, or said DNA encoding said full-length soluble CEACAM8, is contacted with B- or T-cells in combination with other compounds.

3. Method of claim 1, wherein the B- or T-cell expansion takes place in vitro, comprising the steps of:
   a) providing B- or T-cells;
   b) bringing said B- or T-cells in contact with an efficient amount of said full-length soluble CEACAM8, or with said DNA encoding said full-length soluble CEACAM8; and
   c) culturing the B- or T-cells.

4. Method for the diagnosis, monitoring or therapeutic treatment of a condition of a patient in need of immune stimulation comprising administering to the patient full-length soluble CEACAM8 or a DNA encoding said full-length soluble CEACAM8, in an effective amount resulting in B- or T-cell expansion, the condition chosen from the following:
   (a) adoptive immunotherapy;
   (b) immunodeficiency as a result of chronic or acute infection and/or chemo- or radiation therapy;
   (c) human autoimmune diseases, aberrance of the immune response,
   (d) human gout, cancer and/or infection diseases.

5. Method according to claim 4, wherein cancer patients are diagnosed or monitored by labeling neoangiogenetic blood vessels close to tumors by full-length soluble CEACAM8.

6. The method of claim 4 wherein the condition is chosen from (a).

7. The method of claim 4 wherein the condition is chosen from (b).

8. The method of claim 4 wherein the condition is chosen from (c).

9. The method of claim 4 wherein the condition is chosen from (d).

10. The method of claim 4 wherein the condition is human gout and/or infection diseases.

11. Method for prevention of apoptosis in human granulocytes comprising contacting the granulocytes with full-length soluble CEACAM8.

12. Method according to claim 11, adapted for prevention of apoptosis in vitro, wherein the full-length soluble CEACAM8 is human and fused to Fc (full-length soluble human CEACAM8-Fc).

13. Method according to claim 11 for preventing apoptosis in human granulocytes, further comprising incubating a human sample comprising granulocytes with full-length soluble CEACAM8.

14. The method according to claim 13, wherein the full-length soluble CEACAM8 is human and fused to Fc (soluble human CEACAM8-Fc).

15. A method for the therapeutic treatment of a patient requiring immune stimulation comprising administering to the patient full-length soluble CEACAM8 or DNA encoding soluble CEACAM8, in an effective amount resulting in B- or T-cell expansion.

16. A method for the therapeutic treatment of a patient suffering from low B- or T-cell numbers comprising the steps of:
 a) providing B- or T-cells from said patient or from a subject compatible with said patient;
 b) bringing said B- or T-cells in contact with full-length soluble CEACAM8, or with a DNA encoding full-length soluble CEACAM8, in an effective amount resulting in expansion of said cells to expanded B- or T-cells, and
 c) transferring said expanded B- or T-cells to the patient suffering from low B- or T-cell numbers.

* * * * *

UNITED STATES PATENT AND TRADEMARK OFFICE
CERTIFICATE OF CORRECTION

| | | |
|---|---|---|
| PATENT NO. | : 8,501,192 B2 | Page 1 of 1 |
| APPLICATION NO. | : 12/680716 | |
| DATED | : August 6, 2013 | |
| INVENTOR(S) | : Singer | |

It is certified that error appears in the above-identified patent and that said Letters Patent is hereby corrected as shown below:

In the Claims

Column 10, line 65, "YG-051B9" -- should read -- YG-C51B9 --.

Signed and Sealed this
Twenty-fourth Day of November, 2015

Michelle K. Lee
*Director of the United States Patent and Trademark Office*